United States Patent
Herold et al.

(10) Patent No.: US 9,532,751 B2
(45) Date of Patent: Jan. 3, 2017

(54) IMAGING SYSTEM SUBJECT SUPPORT

(71) Applicant: KONINKLIJKE PHILIPS N.V., Eindhoven (NL)

(72) Inventors: Mark Douglas Herold, Stow, OH (US); Ted Alan Bremenour, Concord, OH (US); John Carlon, Madison, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 48 days.

(21) Appl. No.: 14/440,630

(22) PCT Filed: Nov. 14, 2013

(86) PCT No.: PCT/IB2013/060143
§ 371 (c)(1),
(2) Date: May 5, 2015

(87) PCT Pub. No.: WO2014/076658
PCT Pub. Date: May 22, 2014

(65) Prior Publication Data
US 2015/0289826 A1    Oct. 15, 2015

Related U.S. Application Data

(60) Provisional application No. 61/726,181, filed on Nov. 14, 2012.

(51) Int. Cl.
*A61B 6/03* (2006.01)
*A61B 6/04* (2006.01)

(52) U.S. Cl.
CPC ............. *A61B 6/0407* (2013.01); *A61B 6/035* (2013.01)

(58) Field of Classification Search
CPC ..... A61B 6/0457; A61B 6/0407; A61B 6/035; A61B 6/04; A61B 6/0435; A61B 6/0492; A61B 6/547; A61N 5/1049; A61N 5/1081; A61N 5/1069
(Continued)

(56) References Cited

U.S. PATENT DOCUMENTS 4,628,523 A * 12/1986 Heflin ................... A61N 5/10
                                                    250/522.1
5,553,112 A *  9/1996 Hardy ................... A61B 6/08
                                                    378/206
(Continued)

FOREIGN PATENT DOCUMENTS

JP    2008295714 A    12/2008
JP    2009247391 A    10/2009

*Primary Examiner* — David A Vanore

(57) ABSTRACT

Described herein is an approach to determine a deflection of a portion of an imaging system tabletop located at iso-center utilizing a tabletop deflection determiner with a least a first portion located on a rotating gantry portion of the imaging system. In one non-limiting instance, an imaging system includes a rotating gantry portion (606) with an aperture defining an examination region, a tabletop (620) that supports a subject or object in the examination region, wherein the tabletop cantilevers into and deflects in the examination region, and a tabletop deflection determiner (622) that determines a deflection of the tabletop in the examination region, wherein a first portion (702, 706) of the tabletop deflection determiner is located on the rotating gantry portion.

23 Claims, 8 Drawing Sheets

(58) Field of Classification Search
USPC .... 378/65, 20, 209, 17, 196, 205, 21, 4, 68, 378/69; 5/601, 607; 382/131
See application file for complete search history.

(56) References Cited

U.S. PATENT DOCUMENTS

| | | | | |
|---|---|---|---|---|
| 5,751,781 | A * | 5/1998 | Brown | A61N 5/1042 378/65 |
| 8,086,010 | B2 * | 12/2011 | Nabatame | G06T 7/0012 378/21 |
| 8,191,190 | B2 * | 6/2012 | Zapata | A61B 6/0457 378/209 |
| 8,272,088 | B2 * | 9/2012 | Sliski | A61B 5/415 378/209 |
| 2002/0081008 | A1 | 6/2002 | Wollenweber | |
| 2002/0122575 | A1 | 9/2002 | Vaisburd et al. | |
| 2002/0180397 | A1 * | 12/2002 | Henley | A61B 6/0457 318/687 |
| 2006/0093093 | A1 | 5/2006 | Chao et al. | |
| 2006/0184012 | A1 | 8/2006 | Marzendorfer | |
| 2007/0167806 | A1 * | 7/2007 | Wood | A61B 6/032 600/459 |
| 2009/0003522 | A1 * | 1/2009 | Chien | A61N 5/1049 378/65 |
| 2009/0082661 | A1 * | 3/2009 | Saladin | A61B 6/4441 600/415 |
| 2009/0139032 | A1 * | 6/2009 | Bak | A47C 31/123 5/658 |
| 2010/0034435 | A1 | 2/2010 | Kariv | |
| 2010/0287703 | A1 * | 11/2010 | Zapata | A61B 6/5276 5/601 |
| 2012/0093380 | A1 | 4/2012 | Gagnon et al. | |
| 2014/0205059 | A1 * | 7/2014 | Sharpless | A61B 6/035 378/17 |
| 2015/0078514 | A1 * | 3/2015 | Pettinato | A61B 6/0407 378/20 |
| 2015/0126801 | A1 * | 5/2015 | Matteo | F16C 19/54 600/1 |
| 2016/0143607 | A1 * | 5/2016 | Cao | A61B 6/5276 382/131 |

\* cited by examiner

IMAGING SYSTEM SUBJECT SUPPORT

CROSS REFERENCE TO RELATED APPLICATIONS

This application is a national filing of PCT application Serial No. PCT/IB2013/060143, filed Nov. 14, 2013, published as WO 2014/076658 A1 on May 22, 2014, which claims the benefit of U.S. provisional application Ser. No. 61/726,181 filed Nov. 14, 2012, which is incorporated herein by reference.

The following generally relates to a subject support that supports a subject or object in an examination region of an imaging system in a cantilevered position in which a weight of a tabletop of the support and the subject or object thereon causes the cantilevered end of the subject support to deflect, and is described with particular application to computed tomography (CT), but is also amenable to other imaging modalities.

A CT scanner has included a gantry and a subject support. The gantry houses an x-ray tube and a detection system, which are mounted to a rotor, opposite each other, across an examination region. The x-ray tube rotates around the examination region and emits radiation that traverses the examination region and a subject or object disposed therein and illuminates the detection system. The detector system detects the radiation incident thereon and produces projection data indicative thereof. The subject support supports the subject or object in the examination region for the scan.

FIGS. 1, 2, 3, 4 and 5 illustrate an example CT scanner 100 in connection with a subject support 102. FIG. 1 shows a view looking longitudinally along the subject support 102, and FIGS. 2, 3, 4, and 5 show side views. The CT scanner 100 has an aperture that defines an examination region 104. The subject support 102 includes a base 106 and a translatable tabletop 108 that moves between a retracted position (FIG. 2) in which the tabletop 108 is outside of the examination region and an extended position (FIG. 3) in which the tabletop 108 is cantilevered and a sub-portion thereof is inside the examination region 104.

As shown in FIG. 4, a cantilevered tabletop 108 deflects under the weight of at least the tabletop 108. (Note that the deflection is exaggerated for illustrative purposes and does not necessarily represent actual relative deflection.) FIGS. 4 and 5 show the cantilevered tabletop 108 in a non-deflected state with 402 representing the tabletop in a deflected state. The amount of the deflection 404 depends on the weight of the patient (and varies from patient to patient) and a length of the cantilevered portion of the tabletop 108. Unfortunately, the deflection of the tabletop shifts the subject or object off-center (or away from iso-center), which may result in miss-alignment of images during reconstruction, introduction of artifact and degradation of image quality, etc.

Aspects described herein address the above-referenced problems and others.

Described herein is an approach to determine a deflection of a portion of an imaging system tabletop located at iso-center utilizing a tabletop deflection determiner with a least a first portion located on a rotating gantry portion of the imaging system.

In one aspect, an imaging system includes a rotating gantry portion with an aperture defining an examination region, a tabletop that supports a subject or object in the examination region, and a tabletop deflection determiner that determines a deflection of the tabletop in the examination region. The tabletop cantilevers into and deflects in the examination region. The first portion of the tabletop deflection determiner is located on the rotating gantry portion.

In another aspect, a method advancing a tabletop of a subject support into an examination region of an imaging system and measuring a deflection of the tabletop using a tabletop deflection determiner that includes a least a first portion located on a rotating gantry portion of the imaging system.

In another aspect, a computer readable storage medium includes one or more computer executable instructions, which, when executed by a processor of a computing system, causes the processor to: measure a deflection of a portion of an imaging system tabletop located at iso-center utilizing a tabletop deflection determiner with a least a first portion located on a rotating gantry portion of the imaging system.

The invention may take form in various components and arrangements of components, and in various steps and arrangements of steps. The drawings are only for purposes of illustrating the preferred embodiments and are not to be construed as limiting the invention.

FIG. 1 schematically illustrates an example of a prior art imaging system, looking into the examination region.

FIG. 2 schematically illustrates a side view of the example prior art imaging system of FIG. 1 with a retracted tabletop.

FIG. 3 schematically illustrates a side view of the example prior art imaging system of FIG. 1 with an extended tabletop.

FIG. 4 schematically illustrates a side view of the example prior art imaging system of FIG. 1 with a partially extended tabletop with a first deflection.

FIG. 5 schematically illustrates a side view of the example prior art imaging system of FIG. 1 with a partially extended tabletop with a second different deflection.

FIG. 6 schematically illustrates an example imaging system with a tabletop deflection determiner.

FIG. 7 schematically illustrates an example of the tabletop deflection determiner, looking into the examination region.

FIG. 8 schematically illustrates a side view of the tabletop deflection determiner, with a non-deflected tabletop.

FIG. 9A schematically illustrates an example of the tabletop deflection determiner with the tabletop with a first deflection.

FIG. 9B schematically illustrates an example of the tabletop deflection determiner with the tabletop with a second deflection.

FIG. 10 illustrates an example timing diagram for the example tabletop deflection determiner of FIGS. 7, 8, 9A and 9B.

FIG. 11 schematically illustrates another example of the tabletop deflection determiner located under a deflected tabletop that is fully extended.

FIG. 12 schematically illustrates another example of the tabletop deflection determiner located under a deflected tabletop that is partially extended.

FIG. 13 schematically illustrates a variation of the tabletop deflection determiner of FIGS. 11 and 12 in which the tabletop deflection determiner is located within the tabletop.

FIG. 14 schematically illustrates a variation in which the tabletop deflection determiner includes a plurality of reflectors located at different positions along the length of the tabletop.

Figure 1:
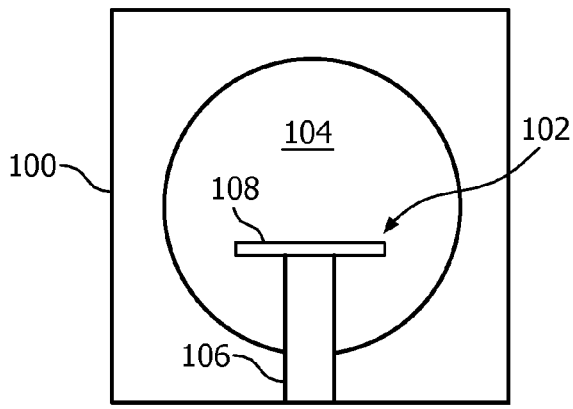
Figure 2:
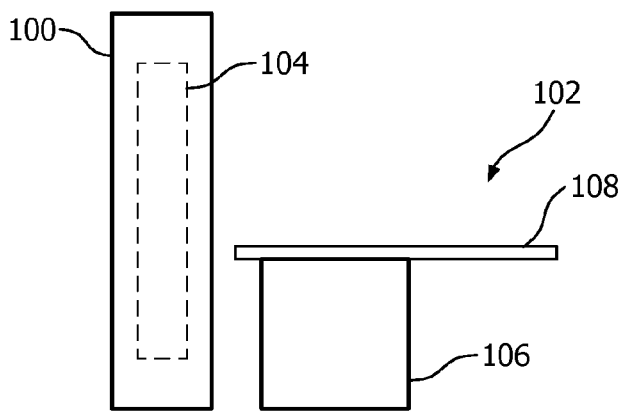
Figure 3:
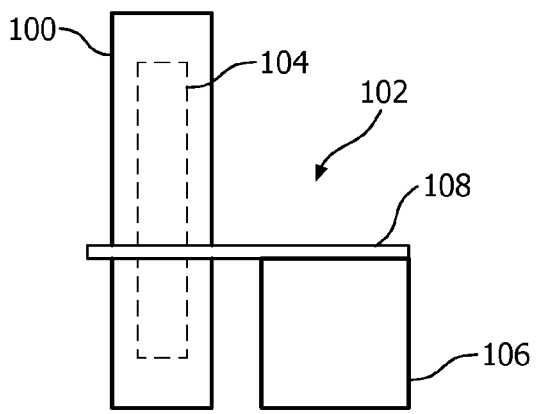
Figure 4:
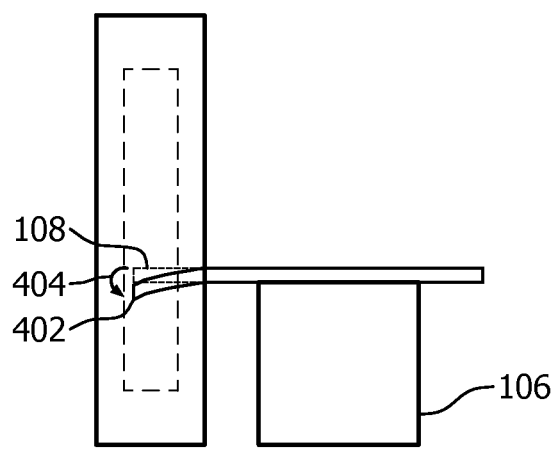
Figure 5:
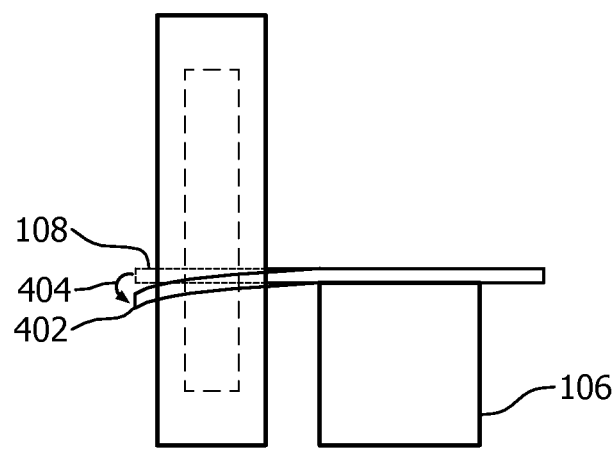
Figure 6:
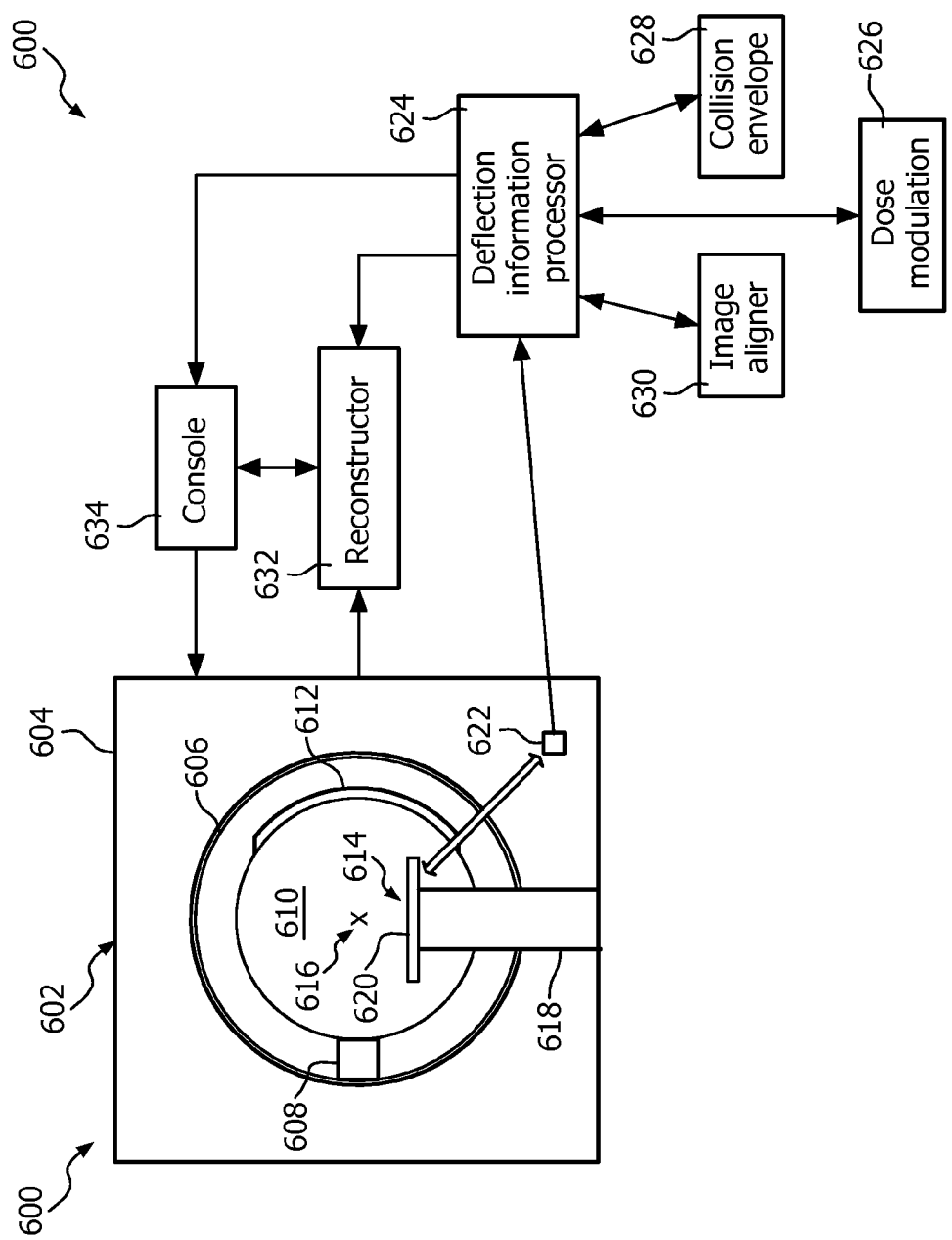

Initially referring to FIG. 6, an imaging system 600 is illustrated. In this example, the imaging system 600 includes a computed tomography (CT) scanner. However, in other embodiments, imaging system 600 includes a magnetic resonance (MR) scanner, a positron emission tomography (PET) scanner, a single photon emission tomography (SPEC) scanner, a hybrid (e.g., PET/CT, PET/MR, etc.) and/or other scanner.

The imaging system 600 includes a gantry 602 with a stationary gantry portion 604 and a rotating gantry portion 606. The rotating portion 606 is rotatably supported by the stationary portion 604.

A radiation source 608, such as an x-ray tube, is supported by the rotating portion 606 and rotates therewith around an examination region 610 (defined by an aperture of the rotating portion 606) about a longitudinal or z-axis.

A detector array 612 subtends an angular arc opposite the radiation source 608, across the examination region 610. The detector array 612 detects radiation that traverses the examination region 610 and generates projection data indicative thereof.

A subject support 614 supports a portion of a subject or object at iso-center 616 in the examination region 610 for scanning. The subject support 614 includes a base 618 and a tabletop 620. The base 618 may be stationary or (vertically and/or horizontally) moveable. The tabletop 620 translates along the base 618, into and out of the examination region 610. The tabletop 620, when cantilevered from the base 618, deflects under the weight of the tabletop 620 and a weight of a subject and/or object (not shown) thereon.

A tabletop deflection determiner 622 determines a deflection of the tabletop 620. As described in greater detail below, in one non-limiting instance, a first portion of the tabletop deflection determiner 622 is located on the rotating portion 606 and a second portion is located on the tabletop 620, and deflection is determined with respect to the rotating gantry 606 and iso-center 616. Also describe below, other configuration are also contemplated herein. The deflection information can be measured during a pre-scan projection or 2D (e.g., surview, pilot, scout, etc.) or volume (low resolution and/or low dose 3D) scan and/or during a volume scan of the subject or object.

A deflection information processor 624 processes the tabletop deflection. In one instance, this includes estimating a weight of a subject or object based on the deflection. Such information can be used to select or determine scan parameters such as a dose modulation profile 626 (e.g., kV and/or mA) for a scan. The deflection information processor 624 may also utilize the deflection to select or determine a collision envelope 628 (e.g., allowable horizontal and/or vertical of the tabletop 620 in the examination region 610) for the scan, an image alignment 630 for reconstructing images, to issue a warning that the subject support 614 is overloaded and/or that there is excessive patient motion, and/or other information. The motion information can also be utilized with a motion correction algorithm.

A reconstructor 632 reconstructs the projection data, generating volumetric image data of the examination region 610. This includes reconstructing the projection data based on the selected and/or determined image alignment 630. This may facilitate aligning images with respect to the iso-center 616 even though the tabletop 620 may be at a different vertical position, for example, due to the deflection, with respect to the iso-center 616 for each image. The image alignment 630 can be used to align images of a same scan as the tabletop advances and deflects more, for images from two different scans (e.g., pre and post therapy), for images from two different modalities (e.g., CT and MR), and/or other images.

A general purpose computing system serves as an operator console 634, which includes human readable output devices such as a display and input devices such as a keyboard and/or mouse. Software resident on the console 634 allows the operator to control operation of the imaging system 600. The illustrated console 634 utilizes the dose modulation 626 and/or collision envelope 628 to determine a dose modulation and/or collision envelope for a scan. The dose modulation 626 may reduce subject dose relative to a configuration in which the dose modulation 626 is not utilized. The collision envelope 628 may facilitate optimizing scan coverage.

The deflection information processor 624 can be implemented via a micro-processors) of a computing system(s) (e.g., computer(s)), which executes a computer readable instruction(s). In one instance, the computer readable instruction(s) is encoded on computer readable storage medium such a physical memory and/or other non-transitory medium. Additionally or alternatively, at least one of the computer readable instructions can be carried by a carrier waver, a signal and/or other transitory medium. The deflection information processor 624 can be part of the console 634 and/or the reconstructor 632 and/or a separate computing system(s).

Figure 7:
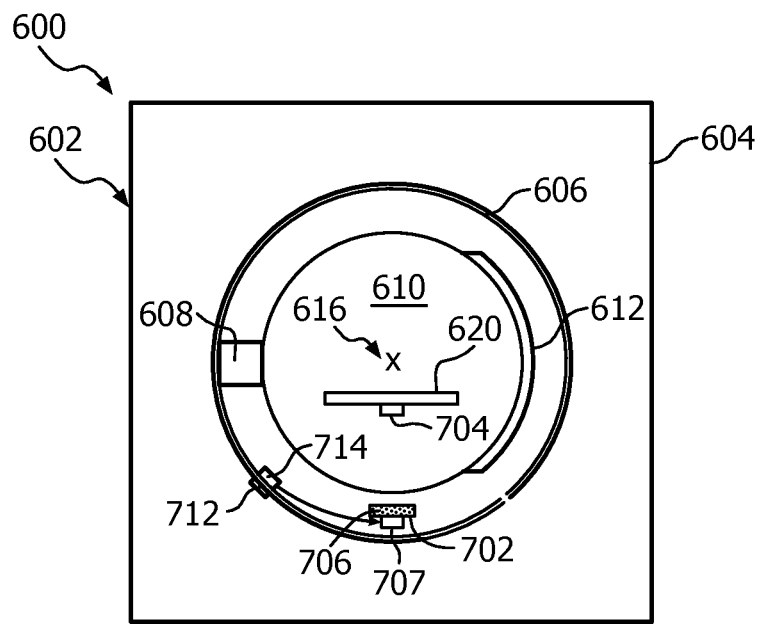
Figure 8:
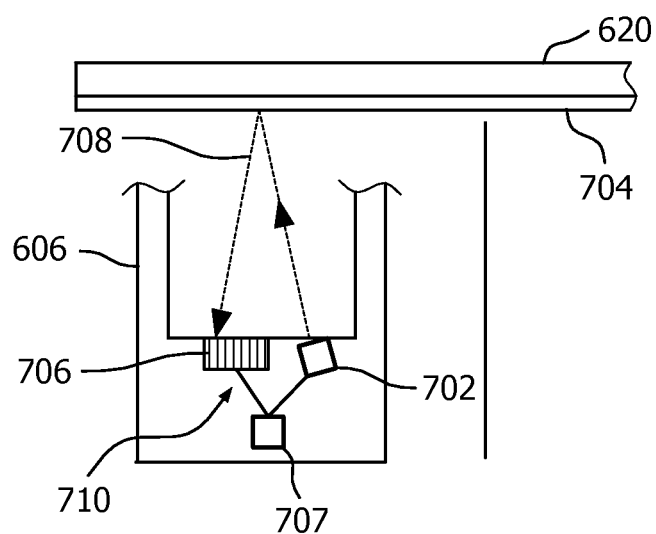
Figure 9A:
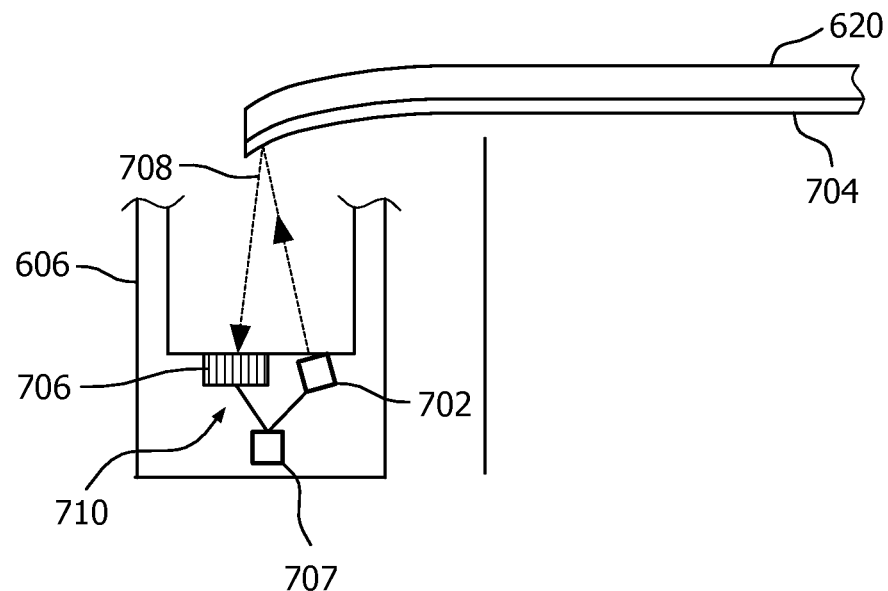
Figure 9B:
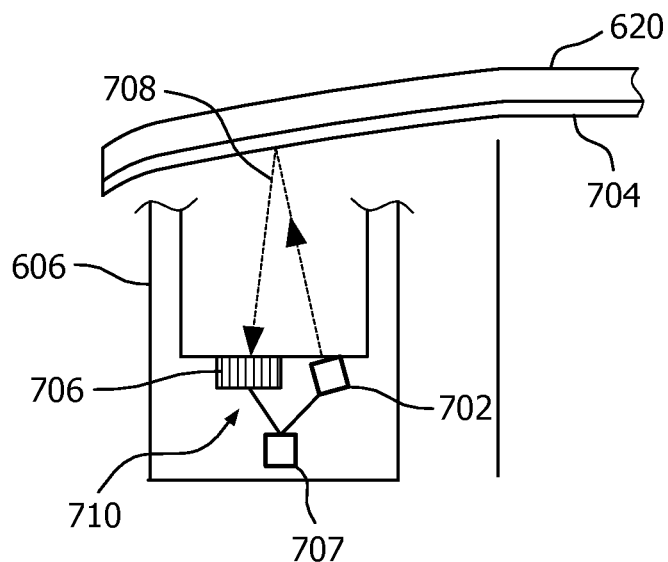
Figure 10:
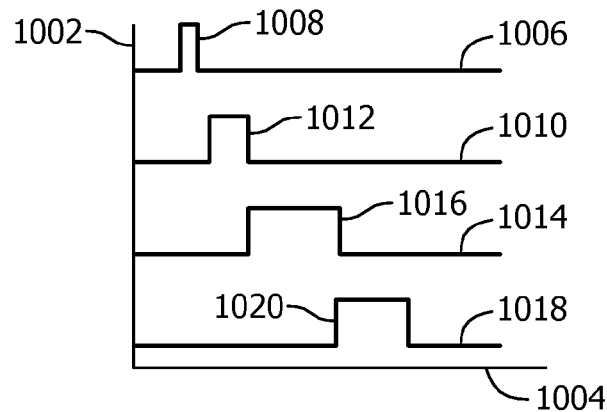

FIGS. 7, 8, 9A, 9B and 10 illustrate a non-limiting example of the tabletop deflection determiner 622. FIG. 7 shows a view looking into the examination region 610, FIG. 8 shows a side view with a non-deflected tabletop 620, FIG. 9A shows the side view with the tabletop 620 with first deflection at iso-center 616, and FIG. 9B shows the side view with the tabletop 620 with further deflection at iso-center 616. FIG. 10 shows a timing diagram.

The tabletop deflection determiner 622 includes an emitter 702, a reflector 704, a sensor 706, and a controller 707. In this example, the emitter 702 can be any point source such as a laser, the reflector 704 is an underside of the tabletop 620, but could also include a reflective paint (e.g., white, including silver, etc.) or film, a mirror, a dichromatic mirror, etc., and the sensor 706 can be an off-the-shelf or other (linear or non-linear) sensor.

The emitter 702 and the sensor 706 are located on the rotating portion 606, and the reflector 704 is located on a side of the tabletop 620 facing away from iso-center 616. The emitter 702 emits a beam 708, which strikes the reflector 704. The reflector 704 reflects the beam 708 towards the sensor 706, which includes a plurality of detector elements 710 that detect the reflected beam 708 and produce a signal.

As shown, an angle of incidence of the beam 708 at the reflector 704 and an angle of reflection at which the beam 708 travels toward the sensor 706 depends on an angular orientation of the emitter 702 with respect to the tabletop 620 and the deflection of the tabletop 620. In FIG. 8, the tabletop 620 is not deflected, and the beam 708 strikes a leftmost element 710 of the sensor 706. In FIG. 9A, the tabletop 620 is just at iso-center 616 with first deflection and the beam 708 strikes a middle element 710. In FIG. 9B, the tabletop 620 is further extended and deflects more than in FIG. 9A and strikes an element 709 on the right side.

The element 709 detecting the beam 708 outputs a signal with peak amplitude indicative thereof. The other elements 709, not detecting the beam 708, either do not out a signal or output a signal with a baseline peak amplitude and/or noise. Where two or more elements 709 detect the signal, each will output a signal with a peak magnitude indicative of an amount of the beam 708 detected thereby. An optical element can be utilized to focus the beam 708 on the sensor 706.

A deflection amount or value can be determined by mapping the element 710 with the peak amplitude to a deflection value (e.g., in units of millimeters). The mapping can be determined during manufacturing, installation, service calls, and/or otherwise. The mapping can be stored in a look up table (LUT) or as a polynomial which can be used to compute the deflection value on the fly. Other approaches to determining the deflection based on the detected signal are also contemplated herein. An example of suitable resolution is on the order of 0.50 millimeters (mm) or less, such as 0.30, 0.25 mm, 0.10 mm, etc.

Generally, as the tabletop 620 deflection at iso-center 616 increases, the beam 708 moves (or walks) from left to right across the sensor 706, illuminating different elements, and as the tabletop 620 deflection at iso-center 616 decreases, the beam 708 moves (or walks) from right to left across the sensor 706, illuminating different elements. The angle between the beam 708 striking the reflector 704 and the beam 708 reflected from by the reflector 704 is proportional (or otherwise mathematically related, in a known or measurable manner) to the deflection of the tabletop 620 at iso-center 616.

The controller 707 controls emission by the emitter 702 and detection by the sensor 706. The controller 707 activates the emitter 702 and the sensor 706 when the emitter 702 is under the tabletop 620. In the illustrated example, at this position, the radiation source 608, the detector array 612 and other components of the imaging system 100 are not in the path from the emitter 702 to the tabletop 620.

Flag and proximity sensors 712 and 714, respectively located on the stationary portion 604 and the rotating portion 606, identify when the emitter 702 is under the tabletop 620 in measurement position and sends a control signal to the controller 707 to active the emitter 702 and sensor 706. The control signal is sent when the flag sensor 714 is adjacent to the proximity sensor 712. Other approaches to identifying an angle at which a measurement is activated area also contemplated herein.

Where the stationary gantry 604 includes an optically transparent or translucent material through which alignment lasers emit alignment beams, the tabletop deflection determiner 622 can be oriented such that the emitter 702 emits the beam 708 through the same material. In one instance, one or more such alignment lasers can also be utilized as the emitter 702. In another instance, the tabletop deflection determiner 622 can be situated with a different optically transparent or translucent material.

FIG. 10 shows a timing diagram for the embodiment of FIGS. 7,8, 9A and 9B. A y-axis 1002 represents magnitude and an x-axis 1004 represents time. A first profile 1006 represents the output of the flag sensor 714, which, in this example, includes a pulse 1008 when the flag sensor 714 is adjacent to the proximity sensor 712. A second profile 1010 shows a sampling period 1012, which is triggered by the pulse 1008. A third profile 1014 shows a data conversion period 1016, triggered by a falling edge of the sampling period 1012, at which the measured signal is converted to a signal to convey to the deflection processor 624. A fourth profile 1014 shows a data transfer period 1020.

It is to be appreciated that having the tabletop deflection determiner 622 located at iso-center, as shown in FIGS. 7,8, 9A, and 9B, the deflection of the tabletop 620 (including deflection of the base 618) and thus the subject or object thereon can be determined with respect to iso-center 616, which is the center of the scan plane, which allows for accurate correction for deflection. However, the tabletop deflection determiner 622 can be shifted off iso-center 616 and still be utilized to correct for deflection.

In addition, the tabletop deflection determiner 622 does not have to be angularly shifted 90 degrees with respect to the source 608 and the detector array 612 (as shown). Furthermore, more than one emitter 702, reflector 704 and/or sensor 706 can be employed.

Variations are discussed next.

Figure 11:
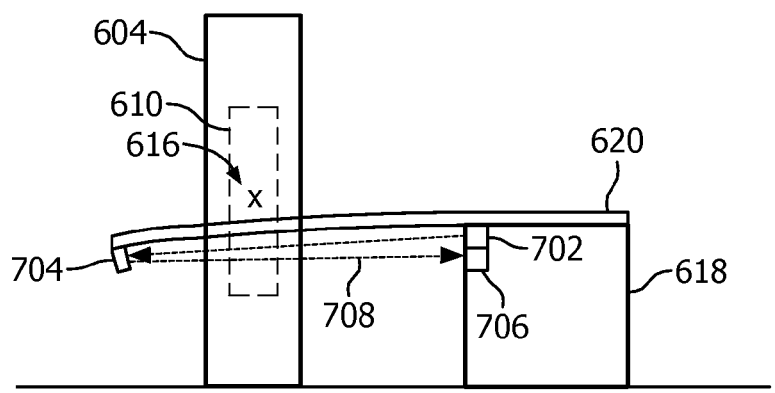
Figure 12:
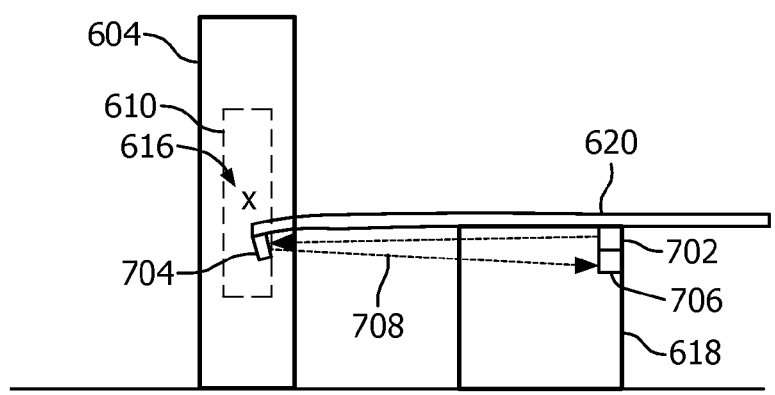

FIGS. 11 and 12 show an embodiment in which the emitter 702, the reflector 704, and the sensor 706 are located under the subject support 614. In this embodiment, the emitter and sensor 702 and 706 are located on a portion of tabletop 620 which generally does not cantilever over the base 618 and thus does not deflect, and the reflector 704 is located at an end of the tabletop 620 that extends into the examination region. Similar to the embodiment described above, the angle of reflection depends on the amount of tabletop 620 deflection and determines which element of the sensor detects the beam 708. This embodiment determines deflection of the end of the tabletop 620, which will not necessarily be at iso-center 616, as shown in FIG. 11.

Figure 13:
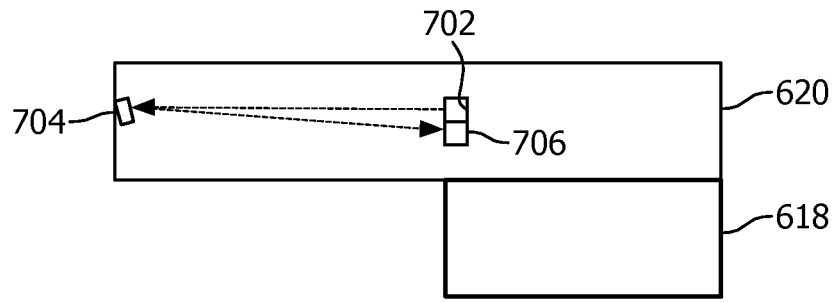

FIG. 13 shows a variation in which the emitter 702, the reflector 704, and the sensor 706 are located within the tabletop 620 of the subject support 614. The emitter 702, the reflector 704, and the sensor 706 can be located within a cavity or material free region in tabletop 620 (as shown), a hollow structure (e.g., a glass, plastic, carbon, etc. tube, box, etc.) located in the tabletop 620, etc. At least one of the emitter 702 or the sensor 706 can alternatively be located in the base 618.

Figure 14:
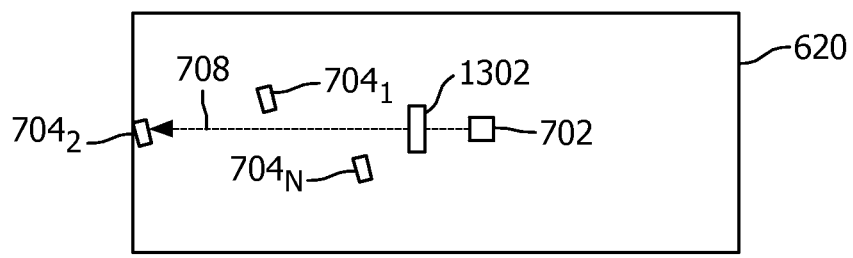

As shown in the top down view of FIG. 14, N (where N is an integer) reflectors $704_1$, $704_2$, . . . , $704_n$, located at different lengths along the long axis, can be used. With this embodiment, the reflector 704 closest to iso-center is used to make the measurement. Alternatively, measurement can be obtained from multiple reflectors, with an average or interpolated value being used to determine the deflection. An optional element 302 can be used to direct, divert, split, etc. the beam 708 based on the reflector 704 being used. Multiple emitters 702 and/or sensor 705 can also be used.

Figure 15:
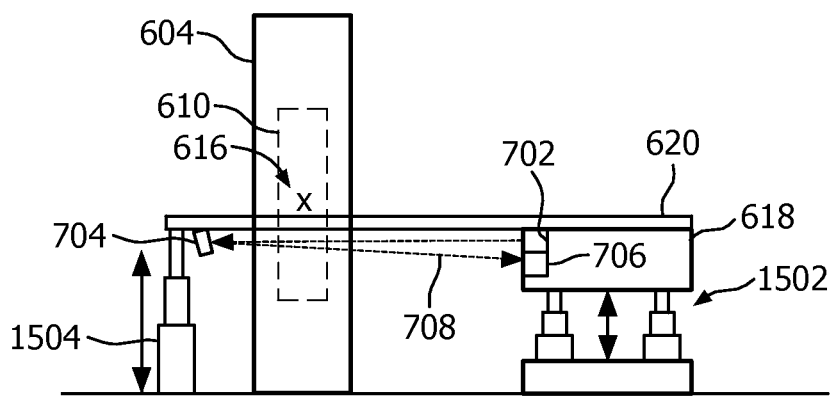
FIG. 15 illustrates an example subject support including actuators for compensating for tabletop deflection.

FIG. 15 shows an embodiment which includes first and/or second sets of actuators 1502 and 1504 configured to raise and lower respective ends of the tabletop 630 based on the deflection of the tabletop 620. Each of the sets of actuators 1502 and 1504 is independently controlled based on the deflection measurement to maintain the portion of the tabletop 620 at iso-center 616 at approximately a same vertical height with respect to iso-center.

In another variation, one or more multipliers (e.g., mirrors) can be used to increase to increase the beams reflected angle. By way of non-limiting example, in a three mirror configuration, the beam 708 would be directed at a first mirror located at the end of the cantilevered portion of tabletop 620. The beam 708 would reflect off of this mirror and travel back to the other end of the tabletop 620, where the beam 708 would reflect off a second mirror. The reflected beam 708 would travel again towards the end of the cantilevered portion of tabletop 620 and reflect off a third mirror, which would reflect the beam 708 towards the sensor 706. In one non-limiting instance, the mirrors would be fixed to the tabletop 620 such that as the tabletop 620 deflects the mirrors' relative position angles change resulting in a suitable beam reflection angle.

In another variation, at least a portion of the tabletop deflection determiner 622 (e.g., the emitter 702 and/or the sensor 706) is located on the stationary portion 604 of the gantry 602.

Figure 16:
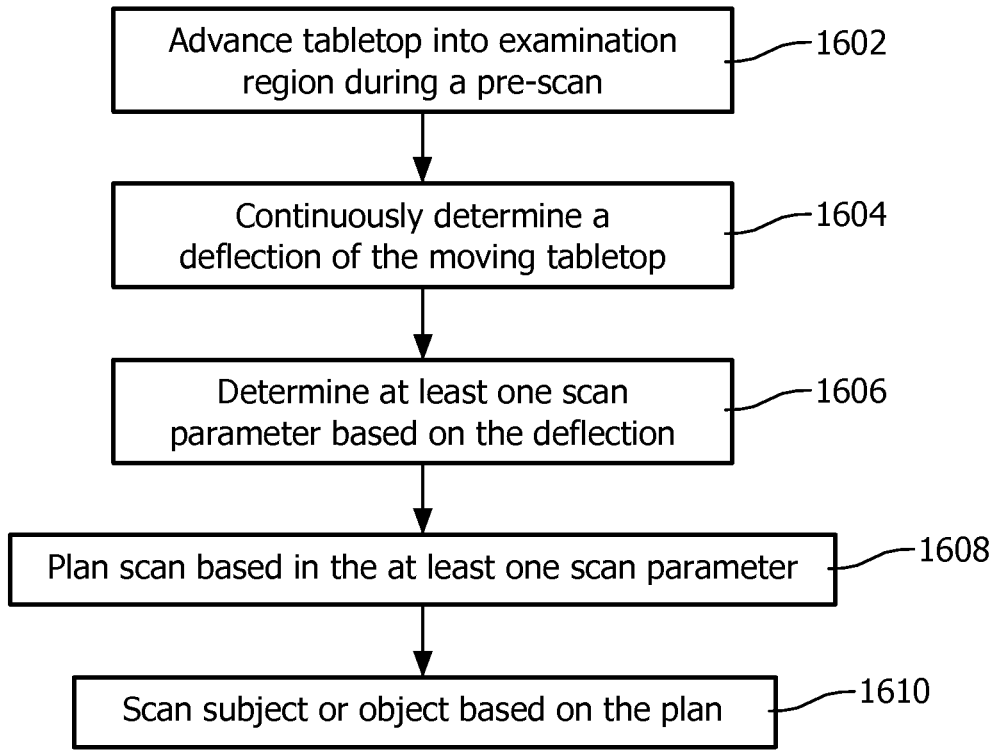
FIG. 16 illustrates an example of method in which tabletop deflection is determined in a pre-scan.

FIG. 16 illustrates a method for determining deflection during a pre-scan of a subject or object.

At 1602, the tabletop 620 advances into the examination region of an imaging system for a pre-scan of a subject or object.

At 1604, a deflection of the tabletop 620 is continuously determined.

At 1606, the deflection is utilized to determine one or more scan parameters such as a dose modulation, an image alignment, and/or a collision envelope.

At 1608, the one or more scan parameters are used to plan a scan of the subject or object.

At 1610, a scan is performed based on the plan.

Optionally, the deflection can be utilized to flag a weight overload.

Optionally, the deflection can be used to detect patient movement. As discussed herein, detected movement can be used to trigger stopping a scan, for example, in order to mitigate dosing a patient when there is too much patient motion to produce diagnostic images.

Figure 17:
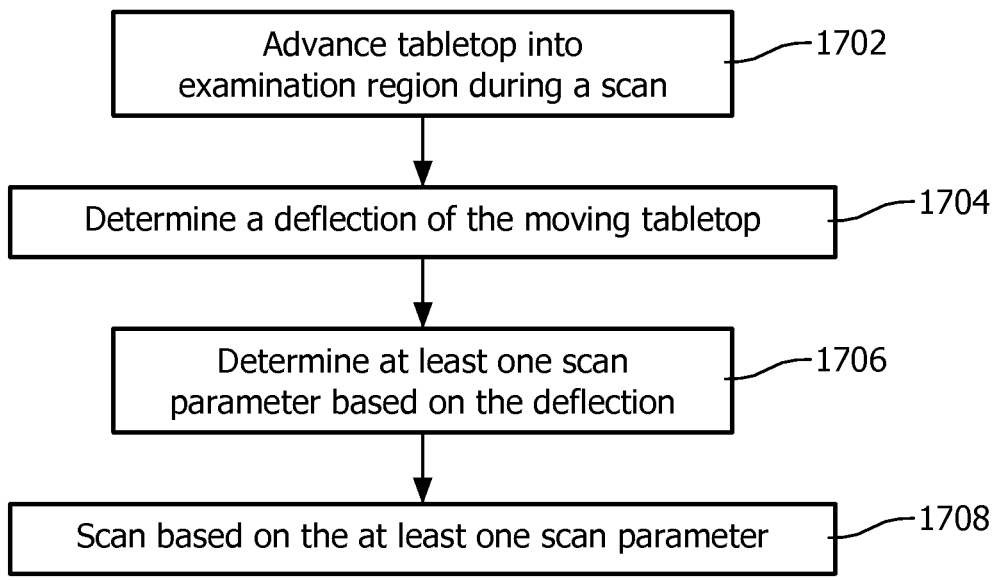
FIG. 17 illustrates an example of method in which tabletop deflection is determined during scanning.

FIG. 17 illustrates a method for determining deflection during a scan of a subject or object At 1702, the tabletop 620 advances into the examination region of an imaging system for a scan of a subject or object.

At 1704, a deflection of the tabletop 620 is determined. The deflection can be measured continuously, with a predetermined frequency, based on the angular position of the rotating portion 606 of the gantry 602.

At 1706, the deflection is utilized to determine one or more scan parameters such as a dose modulation, an image alignment, and/or a collision envelope.

At 1708, the one or more scan parameters are used during the scan of the subject or object to adjust the scan.

It is to be appreciated that the ordering of the acts herein is not limiting. As such, other orderings are contemplated herein. In addition, one or more acts may be omitted and/or one or more additional acts may be included.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
   a rotating gantry portion with an aperture defining an examination region;
   a tabletop configured to support a subject or object in the examination region, wherein the tabletop cantilevers into and deflects in the examination region; and
   a tabletop deflection determiner configured to determine a deflection of the tabletop in the examination region, wherein a first portion of the tabletop deflection determiner is located on the rotating gantry portion and a second portion of the deflection determiner is located on a portion of the tabletop that deflects when the tabletop is in the examination region on a side of the tabletop facing away from iso-center.

2. The imaging system of claim 1, wherein the first portion includes an emitter and a sensor.

3. The imaging system of claim 2, wherein the emitter includes a laser and the sensor includes an array of detector elements.

4. The imaging system of claim 1, wherein the second portion includes a reflector.

5. The imaging system of claim 4, wherein the reflector includes at least one of a reflective paint, a reflective film, a mirror, or a dichromatic mirror.

6. The imaging system of claim 1, wherein the emitter, the reflector and the sensor are arranged with respect to each other so that a beam emitted by the emitter reflects off the reflector and strikes the sensor at a first location on the sensor corresponding to a first amount of deflection and at a second different location on the sensor corresponding to a second different amount of deflection.

7. The imaging system of claim 1, wherein the tabletop deflection determiner is configured to measure the deflection with respect to iso-center.

8. The imaging system of claim 1, further comprising:
   a stationary gantry portion;
   a proximity sensor affixed to the stationary gantry portion; and
   a flag sensor affixed to the rotating gantry portion, wherein the flag sensor is configured to convey a command signal which activates the tabletop deflection determiner in response to the flag sensor being within a predetermined range of the proximity sensor.

9. The imaging system of claim 1, further comprising:
   a deflection information processor configured to process the deflection and determines at least one of a dose modulation profile for the scan, a collision envelope for the scan or an image alignment for reconstruction based on the deflection.

10. The imaging system of claim 9, wherein the deflection information processor is configured to estimate a weight of the subject or object based on the deflection.

11. The imaging system of claim 10, wherein the deflection information processor configured to identify a tabletop weight overload based on the estimate.

12. The imaging system of claim 9, wherein the deflection information processor is configured to estimate a motion of the subject or object on the tabletop based on the deflection.

13. A method, comprising:
   advancing a tabletop of a subject support into an examination region of an imaging system; and
   measuring a deflection of the tabletop using a tabletop deflection determiner that includes a least a first portion located on a rotating gantry portion of the imaging system and at least a second portion located on a portion the tabletop that deflects when the tabletop is in the examination region on a side of the tabletop away from iso-center.

14. The method of claim 13, further comprising:
   acquiring the measurement during a pre-scan of the subject or object.

15. The method of claim 14, further comprising:
   utilizing the measurement to determine at least one of a dose modulation profile, a collision envelope or an image reconstruction alignment for a scan.

16. The method of claim 15, further comprising:
scanning the object or subject based on the at least one of the dose modulation profile, the collision envelope or the image reconstruction alignment.

17. The method of claim 13, further comprising:
acquiring the measurement during a volume scan of the subject or object.

18. The method of claim 17, further comprising:
utilizing the measurement to determine at least one of a dose modulation profile, a collision envelope or an image reconstruction alignment.

19. The method of claim 18, further comprising:
adjusting one or more of the at least one of the dose modulation profile or the collision envelope during the scan based on the deflection.

20. The method of claim 13, wherein the first and second portions are arranged with respect to each other so that a beam emitted by the first portion reflects off the second portion and strikes the first portion at a location of the first portion that is dependent on an amount of the deflection.

21. The method of claim 13, further comprising:
measuring the deflection with respect to iso-center.

22. The method of claim 13, further comprising:
triggering the tabletop deflection determiner to measure the deflection base on a predetermined angular position of the rotating gantry portion.

23. A computer readable storage medium encoded with one or more computer executable instructions, which, when executed by a processor of a computing system, causes the processor to: measure a deflection of a portion of an imaging system tabletop located at iso-center utilizing a tabletop deflection determiner with a least a first portion located on a rotating gantry portion of the imaging system and a least a second portion located on a portion the tabletop that deflect when the tabletop is in the examination region on a side of the tabletop facing away from iso-center.

* * * * *